United States Patent [19]
Larson et al.

[11] 3,950,137
[45] Apr. 13, 1976

[54] APPARATUS FOR MEASURING THE PRESENCE OF A WEAK ACID OR A WEAK BASE IN A LIQUID

[75] Inventors: Thurston E. Larson; Russell W. Lane; Chester H. Neff, all of Champaign, Ill.

[73] Assignee: Illinois State Water Survey of the Department of Registration and Education, Champaign, Ill.

[22] Filed: Oct. 11, 1974

[21] Appl. No.: 514,234

Related U.S. Application Data

[63] Continuation-in-part of Ser. No. 281,778, Aug. 18, 1972, Pat. No. 3,904,365.

[52] U.S. Cl. .............................. 23/253 R; 324/30 R
[51] Int. Cl.$^2$ .................. G01N 27/10; G01N 33/20
[58] Field of Search ....... 23/253 R; 324/30 R, 30 B; 204/1 R, 1 T, 195 R, 195 T

[56] References Cited
UNITED STATES PATENTS

| | | | |
|---|---|---|---|
| 2,559,090 | 7/1951 | Potter | 23/253 R UX |
| 3,531,252 | 9/1970 | Rivers | 23/253 R X |

*Primary Examiner*—Robert M. Reese
*Attorney, Agent, or Firm*—Schuyler, Birch, Swindler, McKie & Beckett

[57] ABSTRACT

A method and apparatus for measuring the presence of a weak acid or weak base in a liquid by withdrawing a sample from the liquid; reacting the sample with an excess amount of strong acid or strong base reagent; measuring the conductivity of the reagent-treated sample and comparing the measured conductivity to a standard value.

15 Claims, 8 Drawing Figures

APPARATUS FOR MEASURING THE PRESENCE OF A WEAK ACID OR A WEAK BASE IN A LIQUID

This application is a continuation-in-part of our copending application Ser. No. 281,778 filed Aug. 18, 1972, now U.S. Pat. No. 3,904,365.

The use of conductivity measurements to determine the composition of liquids is known, as exemplified by U.S. Pat. No. 2,823,673. More recently, methods have been proposed for analyzing the composition of solutions utilizing differential electrical conductivity. Such methods are exemplified by U.S. Pat. No. 3,531,252. Conductivity techniques are highly accurate and conductivity apparatus generally requires only minimal maintenance. However, no conductivity method or apparatus has been available which would satisfactorily measure the presence of a weak acid or weak base in a liquid.

Generally, a substantial portion of a weak acid or weak base in solution is present in un-ionized form. Since the conductivity of a liquid is a function of the ions therein, conventional conductivity methods are unsuited for measuring the amount of un-ionized weak acid or base present in a liquid. Further, although conductivity measurements are generally highly sensitive, quantitative detection of minute quantities of ions resulting from the limited ionization of a weak acid or base in solution is still very difficult.

The alkalinity of water is an important factor in determining whether it will be scale forming or corrosive. In many situations, control of the acidity or alkalinity of a liquid is extremely critical, such as in steam boilers or turbines where deviation from a preferred alkalinity has a corrosive effect on expensive equipment. Thus, the alkalinity of water is an important water property which often requires continuous monitoring to ensure suitability for certain industrial water uses. The determination of alkalinity has heretofore been a laboratory procedure not adaptable for continuous on-site monitoring. In most water supplies, the majority of the total alkalinity results from the presence of $HPO_4^{--}$, $HCO_3^-$, $CO_3^{--}$ and $NH_3$. Due to the low conductivities of such species, direct conductivity measurements of their presence are not practicable.

Also a buffer may be added to the water to resist changes in acidity or alkalinity. A buffer generally consists of two ingredients; a weak acid and a weak base although it is well known that a solution containing only a weak acid or only a weak base may act as buffered solution. When a strong acid is added to a buffered liquid the weak base reacts with the strong acid to produce weaker acid, and less of an increase in acidity of the liquid results than would be produced by the addition of the same amount of strong acid to an unbuffered liquid. Similarly, when a strong base is added to a buffered liquid the weak acid of the buffer reacts with the strong base to produce a weaker base and less of a change in alkalinity of the liquid results than would be produced by the addition of the same amount of strong base to an unbuffered liquid. The capacity of a buffered liquid to resist changes in acidity or alkalinity depends on the absolute amount of the appropriate buffer ingredient, i.e. weak acid or weak base, present in the liquid. Only minimum amounts of buffer are used since large concentrations are undesirable. Consequently the buffer capacity often must be carefully monitored to make certain the buffer ingredients are not exhausted thereby allowing the acidity or alkalinity of the liquid to deviate from the critical range. This requires the ability to accurately measure the presence of small amounts of weak acid or weak base in the liquid.

Accordingly, it is an object of the present invention to provide an improved apparatus for quantitatively determining the presence of a weak acid or a weak base in a liquid.

It is another object of this invention to provide an apparatus for measuring the presence of a weakly acidic or basic chemical in a liquid which utilizes the high mobility of hydronium or hydroxide ions to achieve increased sensitivity.

It is another object of this invention to provide apparatus for determining the alkalinity of a water supply which is not subject to $CO_2$ interference like conventional colorimetric and potentiometric procedures.

It is also an object of this invention to provide apparatus for continuous on-site monitoring of the alkalinity of a water supply which is highly accurate and which requires minimal maintenance.

It is a further object of this invention to provide apparatus for continuously measuring the alkalinity of a water sample which prevents the accumulation of entrained gases which otherwise would cause irregular sample flow.

It is another object of this invention to provide apparatus for continuous measurement of the alkalinity of a water supply which can generate an electrical output signal directly proportional to the sample alkalinity.

It is a further object of the invention to provide apparatus for measuring the total alkalinity or acidity of a water supply due to the presence of small amounts of weak bases or weak acids which will reduce interference from the background conductivity of neutral salts in the water.

These and other objects of the invention are achieved by providing apparatus for measuring the presence of a weak acid or weak base in a liquid by withdrawing a sample of the liquid; mixing the sample with a know amount of a reagent selected from the group consisting of strong acids and strong bases in excess of the amount necessary to completely react with all of the weak acid or weak base therein; measuring the conductivity of the sample and reagent, and comparing the measured conductivity to a standard value, said apparatus comprising a flow line for a sample of water, means to control the rate of flow of a water sample through said line, a first conductivity cell on said line adapted to measure the electrical conductivity of a water sample flowing therethrough, a first fluid inlet downstream from said first conductivity cell for adding a controlled proportion of reagent to a water sample flowing through said line, a second conductivity cell downstream from said first fluid inlet for measuring the electrical conductivity of a water sample flowing through the line after the addition of a controlled proportion of reagent, a second fluid inlet downstream from said second conductivity cell for adding a controlled proportion of liquid to a water sample flowing through the line, a third conductivity cell downstream from said second fluid inlet on said line for measuring the electrical conductivity of a water sample flowing through the line after the addition of a controlled proportion of liquid, and an electronic calculator connected to said first, second and third conductivity cells adapted to compare the conductivity values measured by said conductivity cells and generate an electrical output signal indicative of the composition of a water sample flowing through the line.

Previous apparatus for determining the composition of liquids have measured the conductivity of the ionic components of the liquids directly. As mentioned hereinabove, the total alkalinity of a water results from the presence of weakly basic species which cannot be quantitatively measured by conventional conductivity techniques, and buffers generally include a substantial portion of un-ionized weak acid or base species which cannot be detected by conventional conductivity measurements. Further, the ionized weak acid or base constituents are often large and complex ions which have low mobility in solution or which may form complexes with other ions and consequently have a correspondingly low conductivity. For these reasons, direct conductivity measurements of liquids are inadequate for measurement of buffer capacities or for determining the alkalinity of a water supply.

The invention obviates the above-mentioned problems by providing apparatus for completely reacting the weak acid or base with a reagent selected from the group consisting of relatively strong acids and relatively strong bases. Preferably the acid reagents used in the apparatus of the invention are those which are essentially 100% dissociated in solution such as sulfuric acid, hydrochloric acid and nitric acid, but other relatively strong acids such as phosphoric acid, sulfurous acid, dichloracetic acid, maleic acid, napthalenesulfonic acid, picric acid, oxalic acid, and trichloroacetic acid may also be utilized. The same is true of the base reagents used in the apparatus of the invention. Alkali metal hydroxides are preferred, but other relatively strong bases such as acetamide, pyrazine, and urea may be used. Generally, an acid or base having a dissociation constant greater than about $10^{-2}$ under the prevailing conditions may be suitably utilized in the invention. The term "relatively strong acid or base reagent" as used herein is intended to refer to all such acids and bases. The strong acid or base reagent is added in excess of the amount necessary to completely react with all of the weak acid or base in the liquid, and the conductivity of the resulting solution is measured. An acid reagent is added to the liquid when it is desired to measure the presence of weak base, e.g. the alkalinity of a water or the capacity of a buffer to resist acid, and a base reagent is added to the liquid when it is desired to determine the quantity of weak acid present, e.g. the acidity of a water or the capacity of a buffer to resist basic influences. In this sense a weak base refers to a combination of a strong cation and a weak anion such as $NaHCO_3$, and a weak acid refers to a combination of a weak cation and a strong anion such as $NH_4Cl$.

The apparatus of the invention performs the step of comparing the measured conductivity of a solution containing a weak acid or weak base after the addition of a known amount of a relatively strong acid or strong base with a standard value. The standard value may usually be conviently obtained by measuring the conductivity of a similar solution containing no weak acid or base also treated with the same known amount of strong acid or base reagent. Alternately, the standard may be calculated according to theoretical principles from the characteristics of the conductivity cell and the concentration, charge and mobility factor of the ions in solution. A useful standard value for comparison may also be derived by extrapolation from the initial conductivity of the water sample prior to the addition of any reagent and the initial rate of change of conductivity upon the addition of reagent.

The difference in the conductivity, i.e. conductivity differential, is a direct function of the amount of weak acid or base present in the sample and provides a method of increased sensitivity for this determination. Since some of the hydrogen ions or hydroxide ions added with the aforementioned reagents to the solution containing weak acid or base will be consumed by neutralization reaction with the weak acid or base, the remaining concentration and consequently, the conductivity of the solution after addition of the strong acid or base reagent will be less than the conductivity of the solution also treated with reagent but with no weak acid or base present. While direct conductivity measurements are incapable of accurately detecting un-ionized components in a solution, this apparatus accurately indicates the quantitative presence of all such components which react with a strong acid or strong base.

The electrical conductivity of a liquid is dependent not only on the concentration of the ions in solution but also on the mobility of the ions and increases with increasing ion mobility. Since hydrogen ions and hydroxide ions have the highest mobilities of any ionic substances in an aqueous solution, they also have the highest conductivities of any ion at a given concentration. For example, 0.01 molar solution of hydrochloric acid will have a greater conductivity than a 0.01 molar solution of sodium chloride because hydrogen ions have a higher conductivity than sodium ions. Accordingly, when all other factors are equal, such as applied voltage and distance between electrodes, a lower concentration of hydrogen ions will conduct the same current as a significantly higher concentration of sodium ions. Thus, for a given apparatus having a fixed maximum sensitivity to current, much smaller differences in the concentration of hydrogen ions may be detected than of any other cation, and much smaller differences in the concentration of hydroxide ions may be detected than of any other anion. Application of this principle in the apparatus of the invention results in the ability to measure the presence of a weak acid or base with extreme sensitivity.

The mobility of ions in solution, and consequently their conductivity, varies with changes in temperature. Generally, an increase in temperature will increase the mobility of the ions, and thus the conductivity of a given liquid will increase as its temperature is raised. Accordingly, it may be desirable to control the temperature of a liquid sample when making conductivity measurements to determine the concentration of various components in the liquid. In some of the embodiments of the apparatus of the invention disclosed in this specification the temperature of a liquid sample being tested is maintained at its boiling temperature. If, however, the rate of flow of sample through the apparatus of the invention is sufficiently high that only minimal changes in sample temperature are encountered, then no special measures need be undertaken to control the sample temperature.

The conductivity may be recorded on any suitable recording means, such as a conventional strip chart recorder, and subsequently analyzed by comparison with a table of conductivity differences versus known weak acid or base concentrations. Alternately, in a buffered liquid the conductivity difference may be utilized directly to control the addition of additional buffer to the liquid.

Under some circumstances, sensitivity or accuracy of the measurements is enhanced by degassing the solution, for example to remove dissolved $CO_2$. This may be effected by boiling or by sparging the solution or by other methods. If $CO_2$ is not removed, interference with the measurement of the presence of a weak base in the solution may be prevented by adding sufficient acid reagent to suppress the ionization of the carbonic acid formed by the $CO_2$ in solution.

The apparatus of the invention is not limited to use in aqueous systems; they are effective in an analogous manner in other solvents in which electrical conductivity is a measurable property such as liquid ammonia.

Also, the apparatus is suitable for continuously monitoring flowing liquids. In continuous operations, a liquid sample is continuously or periodically injected into a test stream either before or after addition of the reagent and the conductivity is continuously monitored downstream from the points where the sample and/or reagent are added.

Furthermore, the inventive apparatus is capable of measuring the presence of a weak acid or base even though other ions from neutral salts are present in the sample so long as the background conductivity due to the presence of other ions is taken into account in determining the standard value. One way to achieve this is to base the standard value on a measurement of the initial conductivity of the sample prior to the addition of any reagent.

The invention will be more completely explained hereinafter by reference to an illustrative experiment and by the description of arrangements of apparatus for measuring the buffer capacity of boiler water used to generate steam for a steam turbine power plant, for monitoring the borate content in a nuclear reactor in which boron is employed as a chemical shim or neutron absorber, and for monitoring the alkalinity of a municipal water supply. It is understood, however, that the invention is applicable to any situation where the presence of a weak acid or base in a liquid is to be measured.

BRIEF DESCRIPTION OF THE DRAWINGS

The invention will be described with reference to the following drawings wherein.

DETAILED DESCRIPTION OF THE PREFERRED EMBODIMENTS

Test I

Figure 1:
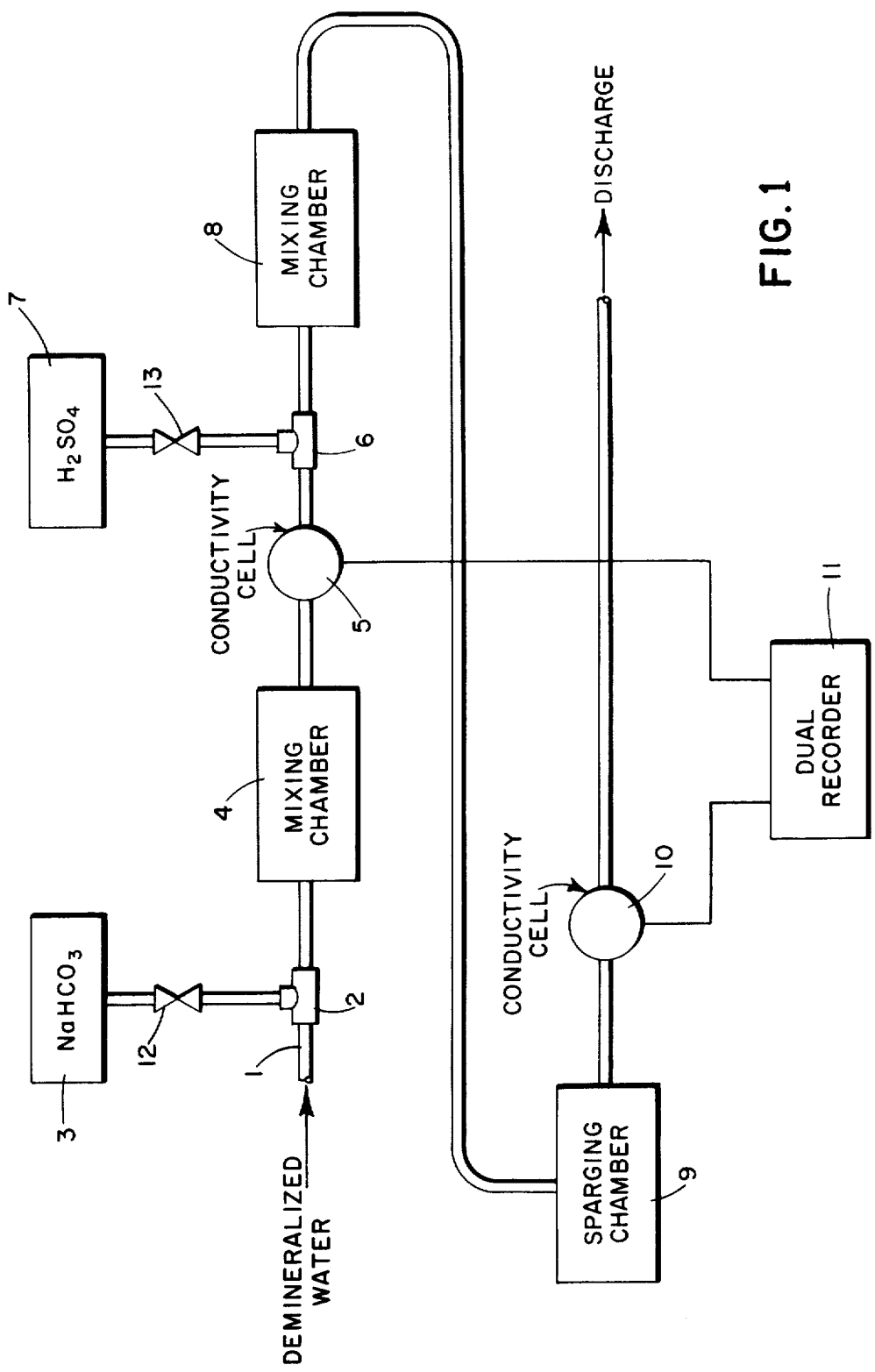
FIG. 1 is a schematic representation of a test apparatus used in an illustrative test to demonstrate the reliability and sensitivity of the invention.
Figure 2:
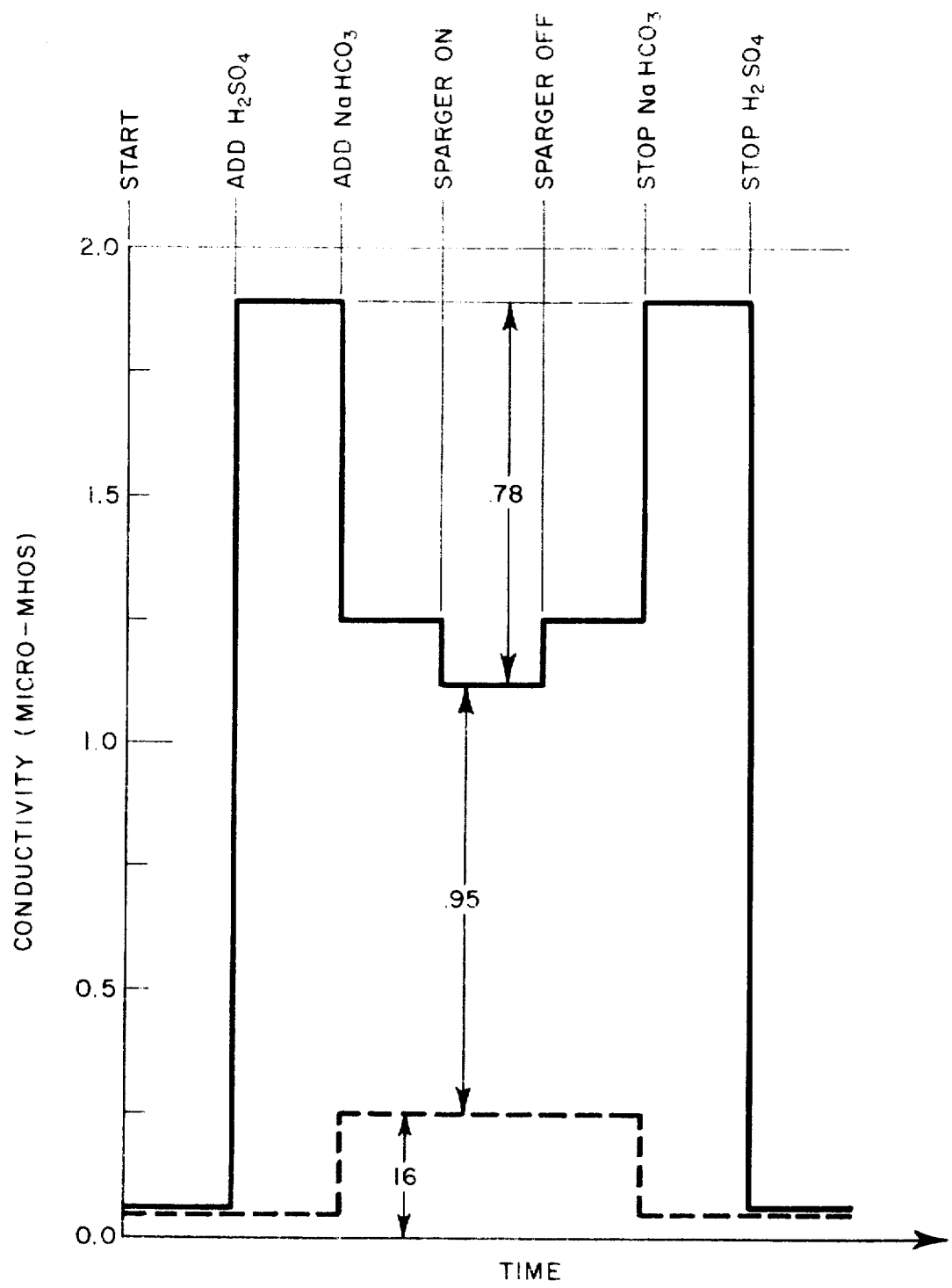
FIG. 2 is a graph showing the results of the illustrative test conducted with the apparatus of FIG. 1.

FIG. 1 is a schematic representation of an experimental arrangement used to illustrate the effectiveness of the present invention. In the experiment sodium bicarbonate served as a weak base and sulfuric acid was used as the reagent. Initially, a flow of de-ionized water was established through conduit 1. The total flow rate was maintained at approximately 310–315 ml. per min. and the temperature of the water was maintained at 20° C. The residual background conductivity of the water was measured by conductivity cells 5 and 10 for comparative purposes and was found to be 0.06 micromhos. Throughout the experiment, the conductivity measurements from both cells were recorded on a conventional dual recorder 11 and are shown graphically in FIG. 2 wherein the dotted line represents the conductivity measurement from cell 5 and the solid line represents the measurement from cell 10. The results are also summarized in Table 1 below:

Table 1

| | Cell 5 Measurement | Cell 10 Measurement |
|---|---|---|
| Start | 0.06 $\mu$ mhos | 0.06 $\mu$ mhos |
| Add $H_2SO_4$ | 0.06 $\mu$ mhos | 1.89 $\mu$ mhos |
| Add $NaHCO_3$ | 0.22 $\mu$ mhos | 1.24 $\mu$ mhos |
| Sparger On | 0.22 $\mu$ mhos | 1.11 $\mu$ mhos |
| Sparger Off | 0.22 $\mu$ mhos | 1.24 $\mu$ mhos |
| Stop $NaHCO_3$ | 0.06 $\mu$ mhos | 1.89 $\mu$ mhos |
| Stop $H_2SO_4$ | 0.06 $\mu$ mhos | 0.06 $\mu$ mhos |

After the residual conductivity was measured, valve 13 was opened to admit a 0.0002N solution of sulfuric acid from tank 7 through T-connector 6 into the water flowing through line 1 at a controlled dilution rate of approximately 1:50. The resulting solution then passed through chamber 8 to ensure uniform mixing. When the addition of acid was begun, the conductivity measurement from cell 10 changed abruptly to 1.89 micromhos while the conductivity measurement from cell 5 remained at 0.06 micromhos. This provided a measure of the conductivity resulting from the addition of the reagent to an unbuffered solution to serve as the standard value. A controlled amount of sodium bicarbonate solution was then introduced into the water from tank 3 through T-connector 2 by opening valve 12 so that the resulting concentration of sodium bicarbonate was about 0.13 parts per million. The sodium bicarbonate solution then passed through mixing chamber 4. The change in conductivity measured by cells 5 and 10 each provide a measure of the amount of sodium bicarbonate added. After the addition of sodium bicaronate was commenced, the conductivity measurement from cell 5 increased from 0.06 micromhos to 0.22 micromhos, a change of 0.16 micromhos. The conductivity measurement from cell 10 dropped from 1.89 micromhos to 1.24 micromhos. A further slight decrease in the conductivity measurement from cell 10 from 1.24 micromhos to 1.11 micromhos was effected by bubbling $CO_2$-free gas through the solution in sparging chamber 9 to remove dissolved carbon dioxide produced by the neutralization of the bicarbonate ions. This gave a total conductivity change of 0.78 micromhos when the invention was used to measure the sodium bicarbonate content of the solution as compared to a change of only 0.16 micromhos when the conductivity of the sodium bicarbonate was measured directly. Significantly, the change in conductivity caused by the sodium bicarbonate when the acid reagent was present was almost five times as great as when no acid was added. This clearly demonstrates the increased sensitivity achieved by the invention.

Figure 3:
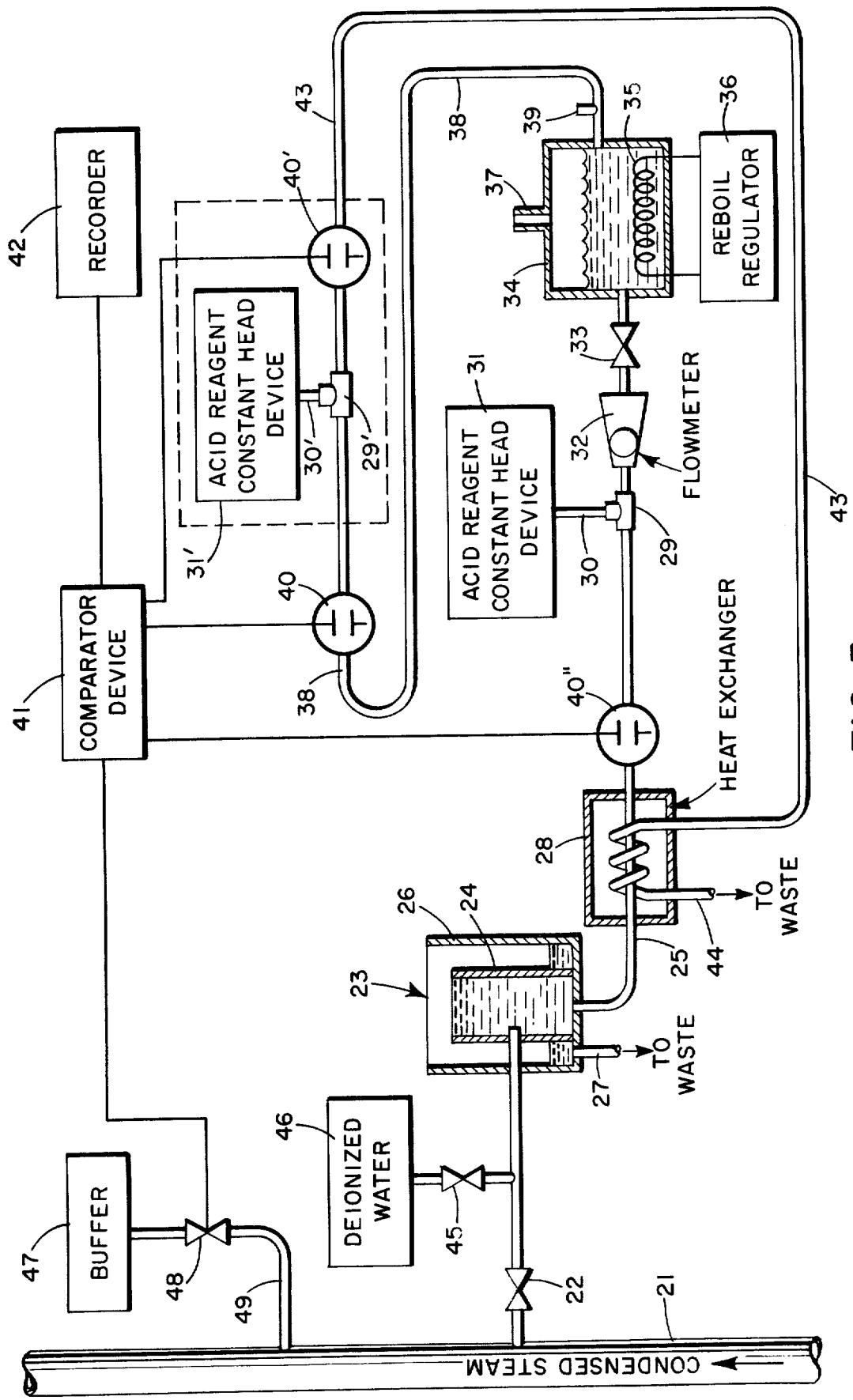
FIG. 3 is a schematic representation of an apparatus suitable for monitoring the buffer capacity of boiler water condensate.

FIG. 3 is a schematic representation of an apparatus for quantitatively measuring the presence of the basic buffer ingredient in a slightly buffered alkaline water source such as a boiler condensate return line. A sample of the condensate is withdrawn from return line 21 through valve 22 and passed to a constant head device designated by the numeral 23. The constant head device comprises an inner chamber 24 connected to outlet line 25 and an annular outer chamber 26 connected to waste line 27. The sample feed rate to chamber 24 is slightly greater than the outflow rate through line 25 so that a small portion of the sample overflows chamber 24 to waste thereby maintaining a constant head on the main portion of the sample which flows out through line 25 to heat exchanger 28 where it is preheated by effluent from the conductivity cell. The sample then flows to mixing tee 29 where it is mixed with a controlled proportion of a strong acid reagent brought in through line 30 from constant reagent head device 31. The proportion of reagent supplied must be in excess of the amount required to react with all of the buffer ingredient in the sample. After mixing with the acid, the sample solution passes through flowmeter 32 and valve 33 to a stainless steel chamber 34. The flowmeter and its associated valve are used to maintain a constant flowrate of treated sample into the chamber. An electrical immersion stainless steel heater 35 in chamber 34 is used to heat the reagent-treated sample to boiling. Boiling is a convenient manner of degassing the solution and of maintaining a constant temperature. A conventional reboil regulator 36 associated with heater 35 adjusts the heating of the sample to maintain a plume of steam from vent 37 in chamber 34. The heated sample leaves chamber 34 through line 38, which is preferably vented as at 39 to prevent syphoning of the sample from chamber 34 thereby maintaining the level in the chamber, and passes to conductivity cell 40 where the conductivity of the treated sample is measured. The conductivity measurement is sensed by comparator device 41 which compares the measured value to a standard calibrated in a manner described hereinafter. The difference between the measured and standard values is recorded on a strip chart recorder 42. After the conductivity is measured, the sample flows through line 43 to heat exchanger 28 where some of its heat is transferred to the incoming sample stream before being discharged to waste at 44.

The standard used in the comparator device 41 may be calibrated by closing valve 22 to shut off the flow of sample to the system and opening valve 45 which communicates with a supply of deionized water 46. The deionized water then flows through the system under the same conditions of flow, temperature, pressure and reagent application as did the condenser water. The conductivity of the deionized water plus added reagent is measured as before by conductivity cell 40 and the result of the measurement is again passed to the comparator. Since the conductivity of the deionized water plus the reagent should approach theoretical values, the standard in the comparator is adjusted by means of a variable resistor until the measured value and the standard are balanced, and zero buffer is indicated on the recorder. After the calibration is completed, valve 45 is closed and valve 22 is reopened to resume monitoring of the buffer capacity of the boiler condensate sample stream. The difference between the conductivity of the reagent-treated boiler condensate sample and the standard, i.e. the conductivity of the reagent-treated deionized water, indicates the quantity of buffer in the boiler condensate.

Alternatively, a standard buffer solution may be used in place of the deionized water in the calibration operation. The difference in conductivities then indicates the deviation of the boiler condensate buffer content from the standard instead of the absolute amount of the buffer in the condensate. If desired in situations where buffer is continuously added to the boiler feed water supply, the signal from comparator device 41 may be used to control the addition of buffer from a buffer supply 47 to the stream flowing through line 21 by means of a solenoid valve 48 interposed in connecting line 49.

It is also possible to derive the standard value from a measurement of the conductivity of the sample prior to the addition of the reagent. For this purpose a conductivity cell 40'' may be included on line 25 upstream from the acid reagent source analogous to conductivity cell 5 in FIG. 1.

FIG. 3 also shows an optional arrangement which is useful for confirmatory purposes and provides for increased accuracy. A second controlled amount of reagent is added to the stream flowing through line 43 from acid reagent constant head device 31' through line 30' and mixing tee 29'. The conductivity of the sample stream is again measured by conductivity cell 40' and the result passed to comparator 41 for comparison with a second standard value. It is expressly contemplated that the second standard value could be equal to the first standard value. The addition of a second increment of reagent and the second conductivity measurement are useful to confirm that the reagent supply system is operating properly and that all of the weakly acidic or basic chemical in the sample was completely reacted by the first increment of reagent. The second reagent addition and measurement also enable determination of the rate of change of conductivity upon the addition of excess reagent which varies depending on the different species present in the solution thereby making it possible for the apparatus to compensate for the background conductivity and interference resulting from the presence of other species such as sulfate salts in the sample in order to achieve increased accuracy. Possibly, there could be a series of three, four or even more sequential additions of reagent each followed by a subsequent measurement of the conductivity. Different reagents could be added at any of the successive points.

Figure 4:
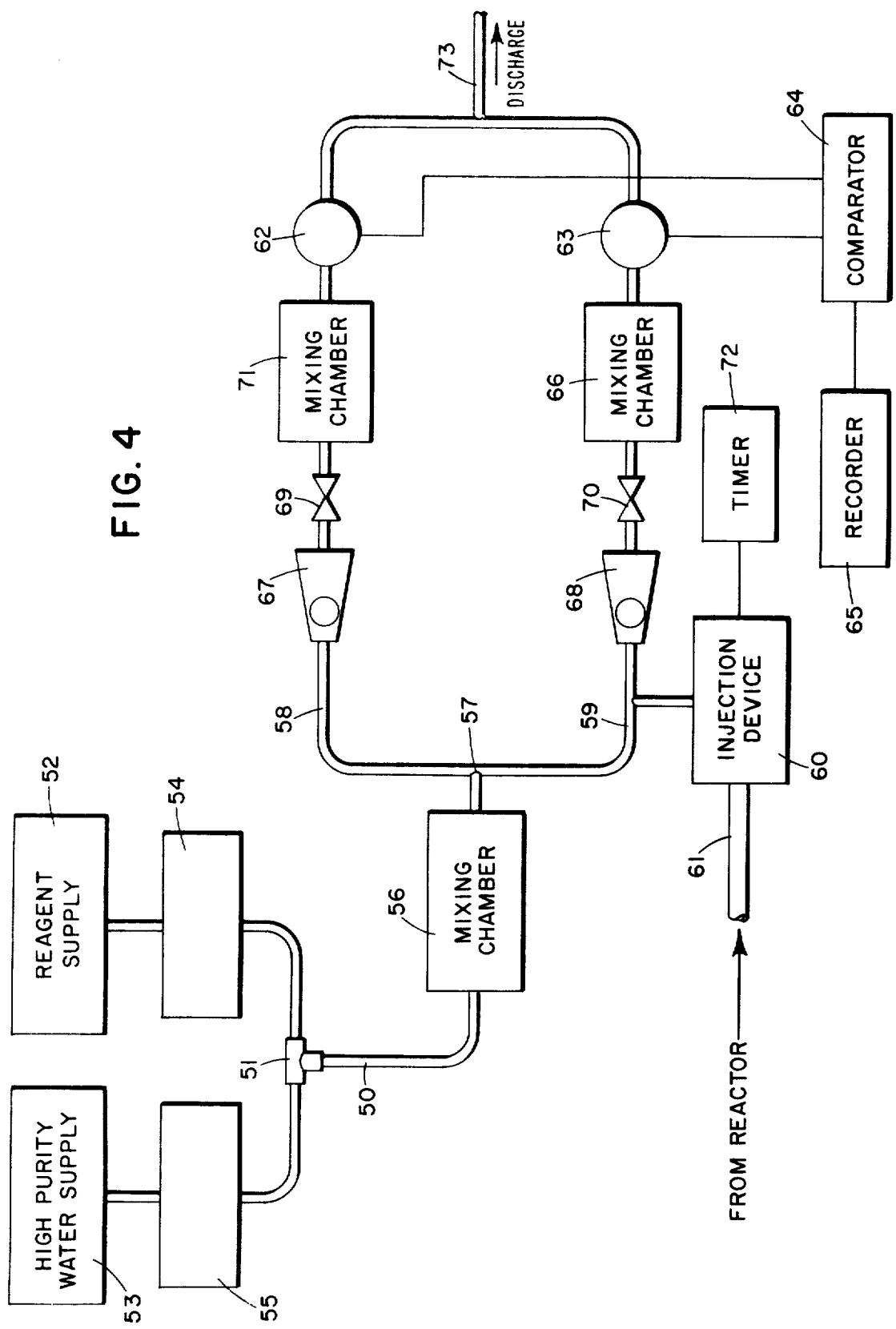
FIG. 4 is a schematic representation of an apparatus suitable for measuring the boric acid concentration in a solution used as a neutron absorber in a nuclear reactor.

A further apparatus is illustrated schematically in FIG. 4. This arrangement is adapted for situations where for economic or other reasons only very small amounts of sample are used. This arrangement also conserves the amount of reagent required in the measurement operation if the concentration of weak acid or base in the sample being measured is quite high. For example, this arrangement is useful in measuring boric acid used in nuclear power plants in concentrations on the order of 2500 ppm. Numeral 50 designates a conduit in which a flow of highly pure strong base reagent is established. The basic reagent may be provided by diluting a standard reagent solution with deionized or distilled water in mixing tee 51. The reagent supply 52 and the high purity water supply 53 may be provided with constant head devices 54 and 55 respectively to ensure uniform dilution of the reagent. Alternatively a small volume pump may be used to feed the reagent into the high purity water line at a controlled rate. A mixing chamber 56 may also be inserted into the line to ensure uniform mixing. The reagent flow is split into two streams at 57 which flow through lines 58 and 59. An injection device 60 withdraws a small sample of borate solution from the reactor through line 61 and injects it into line 59. The volume of the injected sample must be negligible compared to the volume of reagent flowing through line 59 to avoid distortion of the results due to dilution. Alternately, an amount of deionized water equal to the volume of the sample could be added to the stream flowing through line 58 to equalize the dilution. It is of course essential that the strong base flowing through line 59 be in excess of the amount required to completely react with all of the boric acid in the sample injected into the line. The two streams then flow to conductivity cells 62 and 63 where the conductivity of each is measured. The results of the two measurements are sensed by comparator device 64 which compares them and provides a signal to recorder 65 to indicate the difference in conductivity. The two streams are then discharged as at 73.

A mixing chamber 66 may be provided on line 59 to facilitate complete mixing of the sample and reagent. To ensure the two conductivity measurements are strictly comparable, it is desirable to equalize the flows through lines 58 and 59. For this purpose flowmeters 67 and 68 and control valves 69 and 70 are inserted in lines 58 and 59 respectively and a chamber 71 identical to mixing chamber 66 is inserted in line 58.

To further conserve on the amount of sample and reagent utilized, the operation of injection device 60 may be controlled by a timer 72 to provide for intermittent injection of a controlled volume of sample into line 59. The concentration of reagent may be reduced so long as chamber 66 contains a controlled excess of the reagent each time a sample is injected. The boric acid quickly reacts with the basic reagent in chamber 66 producing a temporary decrease in conductivity sensed by conductivity cell 63 which shows up as a peak on recorder 65. In either the direct or intermittent methods of operation, the recorder may be calibrated to provide a direct readout in concentration of boric acid in the sample being measured by injecting standard samples of known concentration through the system With a little modification, the apparatus shown in FIG. 4 can also be utilized to advantage to inject a controlled excess of reagent into a flowing sample stream instead of injecting a sample into the reagent stream as shown in FIG. 4. This technique eliminates distortion due to background conductivity of the sample.

Figure 5:
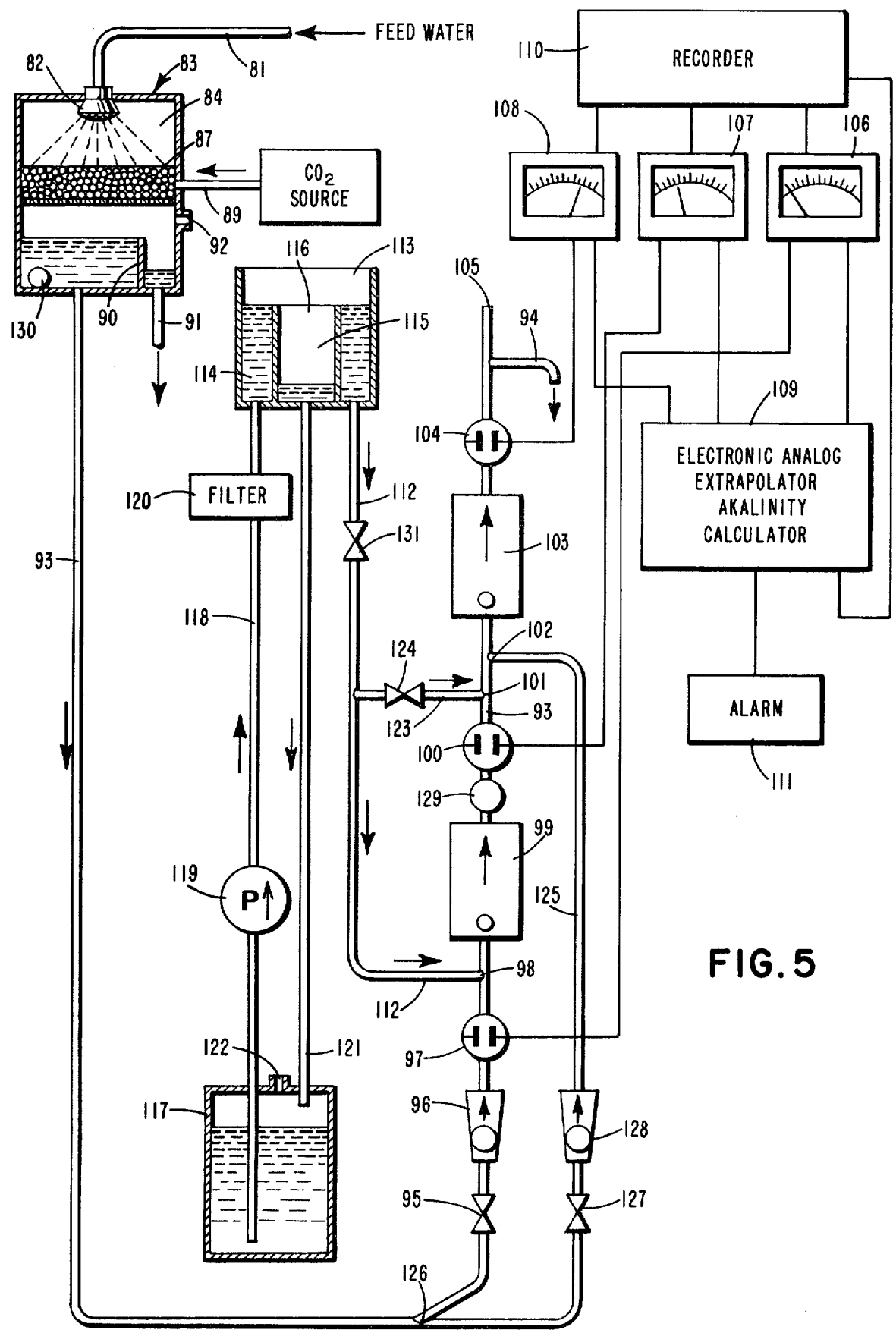
FIG. 5 is a schematic representation of an apparatus for measuring the alkalinity of a water supply.

FIG. 5 illustrates an apparatus for monitoring the alkalinity of a municipal water supply down to less than 10 ppm expressed as $CaCO_3$. A sample of the water is passed through a feed line 81 and a spray nozzle 82 into a carbonating device generally designated by reference numeral 83 comprising an upper chamber 84 and a lower chamber 85 separated by a foraminous member 86. A bed of dispersing media, such as small glass beads 87, is disposed on top of foraminous member 86, and carbon dioxide from a $CO_2$ source 88 is fed through a connecting line 89 into the separating media bed. The water is carbonated as it gravitates through the media bed and the foraminous member into lower chamber 85. An overflow partition 90 separates the main body of chamber 85 from an overflow line 91 so that when the carbonated water sample reaches a depth equal to the height of the partition, the excess will flow over the partition and out the overflow line so that a constant head of water sample is maintained in chamber 85. A gas vent 92 prevents the buildup of superatmospheric pressures within the carbonator.

Sample water from carbonator 83 passes from lower chamber 85 through a flow line 93 to a discharge point 94. It is convenient to cause the sample to flow through line 93 under the influence of gravity by disposing outlet 94 and all parts of line 93 lower than chamber 85. The heights of chamber 85 and outlet 94 are adjustable relative to each other so that the sample head may be varied in order to achieve the desired sample rate of flow through the apparatus. In the illustrated apparatus, the sample head can be varied from about 3 to about 12 inches of water in order to achieve a constant flow rate in the range from 250 to 300 ml per minute. Line 93 includes a vertically oriented segment on which are mounted successively along the path of flow, a valve 95, a flowmeter 96, a first conductivity cell 97, a first fluid inlet 98, a first mixing chamber 99, a second conductivity cell 100, a second fluid inlet 101, a third fluid inlet 102, a second mixing chamber 103, a third conductivity cell 104 and a gas vent 105. Conductivity cells 97, 100 and 104 are connected respectively to conductivity meters 106, 107 and 108. Suitable conductivity meters are Model RA5 Solumeters with 100 mv. outputs manufactured by Beckman Instruments, Inc. The three conductivity meters are in turn connected to an electronic analog computer 109 programmed to calculate the total alkalinity of the water from the three measured conductivity values. In the preferred embodiment illustrated, the computing apparatus and the three conductivity meters are all connected to a multiple chart recorder 110 such as a Model VKP potentiometric chart recorder manufactured by Beckman Instruments, Inc. in order to provide a permanent graphic record of the sample alkalinity. The output of calculator 109 may also be utilized to control an output device 111 which may be any of a number of types of apparatus such as an alarm system, a shut-off mechanism or an apparatus for automatically adding treatment chemicals.

Fluid inlet 98 is connected to an acid reagent delivery system via reagent delivery line 112 which leads from a reagent constant head device 113. Reagent constant head device 113 comprises an annular supply chamber 114 and a return or overflow chamber 115 separated by a partition 116 which controls the depth of the reagent. As with the sample constant head device 83, the height of the reagent constant head device is adjustable with respect to the height of outlet 94 in order to facilitate adjustment of the head of reagent in order to control the rate of flow of reagent through the apparatus. In the apparatus of FIG. 5, the reagent head may be adjusted up to about 10 inches of water. Reagent from a reservoir 117 is continuously pumped to supply chamber 114 through a fill line 118 by means of a pump 119. A filter 120 is interposed in line 118 to assure that the reagent is free of solid contaminants. Reagent is pumped to supply chamber 114 at a higher rate than it is withdrawn through line 112, and the excess flows over the top of partition 116 into return chamber 115 and is returned to the reagent reservoir 117 through a return line 121. It is desirable to have the reagent reservoir vented as shown at 122 in order to maintain the reagent supply at atmospheric pressure and ensure a continuous ready flow of reagent.

Reagent supply line 112 is also connected to fluid inlet 101 on line 93 by means of a line 123, and a valve 124 is provided on line 123 in order to enable regulation of the flow reagent therethrough.

A bypass line 125 running from a fork 126 located in line 93 upstream of valve 95 to fluid inlet 102 is provided in the apparatus. Disposed on bypass line 125 are a control valve 127 and a flowmeter 128 to facilitate regulation of the flow of water sample therethrough. Bypass line 125 makes it possible to dilute a sample flowing through line 93 with an additional amount of sample water after the original sample has been treated with reagent through fluid inlet 98 and the conductivity of the thusly treated sample has been measured by conductivity cell 100. The purpose of such an arrangement will be explained more fully hereinafter in conjunction with an alternate mode of operation of the apparatus.

The basic mode of operation of the device is as follows. A water sample is passed through line 81 and sprayed by means of spray head 82 into the upper chamber 84 of carbonating apparatus 83. At the same time, carbon dioxide from source 88, which may be a tank of compressed $CO_2$, passes through line 89 and enters chamber 84 beneath the surface of the bed of separating media 87 disposed therein. Carbon dioxide dissolves in the water sample as it trickles down through the separating media, whereby all more strongly basic ions in the water react with the carbonic acid formed by the dissolving $CO_2$ to form bicarbonate ions, so that the pH of the sample is adjusted to a range of about 5 to 8, most preferably from 7 to 8, and the total alkalinity of the feed water sample is converted to a single ionic species. The reaction with hydroxide ion may be visualized as follows:

$CO_2 + H_2O \rightarrow H_2CO_3$

$H_2CO_3 + OH^- \rightarrow HCO_3^- + H_2O$

The reaction with carbonate ion is depicted by the following equations:

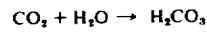

$CO_2 + H_2O \rightarrow H_2CO_3$

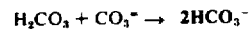

$H_2CO_3 + CO_3^- \rightarrow 2HCO_3^-$

A pH sensor 130 may be included in chamber 85 to monitor the $CO_2$ addition. After the conversion of the total alkalinity of the water sample into a single ionic species, namely bicarbonate ion, the water sample will exhibit a substantially uniform rate of change of conductivity upon the addition of a given strong acid reagent thereto until the total alkalinity of the water is exhausted. For nearly all waters containing bicarbonate ion this rate of change is nearly constant and amounts to approximately 0.65 micromho per cm per ppm. A variable resistance may be included in the electronic circuitry of the analog calculator in order to adjust for other rates of conductivity change should they be encountered.

Where only a single species is likely to be encountered in the water supply so that the rate of change of conductivity upon the addition of reagent will be uniform until the alkalinity of the water is exhausted, the carbonator 83 may be dispensed with and replaced by a simple constant head device such as 23 in FIG. 3.

The carbonated water sample gravitates into lower chamber 85 where it accumulates until the depth of sample in the chamber is equal to the height of partition 90 at which time the excess amount flows over the top of the partition and out discharge line 91. Sample water is continuously withdrawn from chamber 85 through line 93. The rate of flow through the line may be precisely controlled by adjusting the head of the sample and also by means of valve 95. Flowmeter 96 enables a precise determination of the flow rate of the sample. In the normal mode of operation, valve 127 is maintained in the closed position so that none of the feed water sample can bypass conductivity cells 97 and 100 and fluid inlets 98 and 101.

The background conductivity of the sample is measured by conductivity cell 97 and the resulting measured value is passed via conductivity meter 106 to analog calculator 109, and also is recorded by multiple chart recorder 110.

Reagent reservoir 117 is filled with a strong acid reagent, i.e. a solution of known concentration of an acid which is essentially 100% in dissociated or ionic form in solution. Hydrochloric acid is the preferred reagent although other strong acids such as sulfuric or nitric may also be utilized. The reagent concentration must be maintained strictly uniform and must be precisely known. Reagent pump 119 is started so that a continuous supply of the reagent is pumped to supply chamber 114. The reagent then passes from supply chamber 114 through supply line 112 and fluid inlet 98 into the water sample flowing through line 93. Valve 124 is opened so that reagent is also transmitted through line 123 and fluid inlet 101 into the water sample.

The rate of reagent addition may be precisely controlled by appropriate selection of the size of the capillary inlet orifices in fluid inlets 98 and 101 and by appropriate regulation of the head of reagent in the reagent supply system. Accordingly, a carefully controlled, known proportion of acid reagent is added to the flowing sample at each fluid inlet. An optional valve 131 may be included in line 112 to facilitate further control of the rate of flow of the reagent. Valve 131 also allows the reagent supply to be conveniently shut off so that the apparatus can be cleaned.

The amount of acid added at fluid inlet 98 must be sufficient to completely react with all of the bicarbonate present in the solution, thus the amount of reagent added must be greater than the equivalent alkalinity of water sample. A 20% excess over the maximum alkalinity is preferred. An optional pH sensor 129 may be included on line 93 to monitor the reagent addition. Most preferably, sufficient acid reagent will be added to reduce the pH of the sample to at least 3.5 so that ionization of the carbonic acid produced by the neutralization of the bicarbonate ions by the acid reagent will be suppressed. This prevents distortion of the alkalinity measurement by ionization of the carbonic acid. Alkalinity determinations by conventional colorimetric or potentiometric techniques must be corrected for such distortion. For measuring the alkalinity of a municipal water supply in the 10 to 200 ppm range expressed as $CaCO_3$ where the water sample flow rate was approximately 300 ml. per min., a 0.3 ml. per min. reagent flow rate of 3 Normal hydrochloric acid at each injection point is satisfactory.

Mixing chamber 99 is provided in order to ensure complete mixing of the water sample and the added reagent. A suitable mixing chamber may comprise the body of a 100 or 200 ml. pipette with a glass bead inserted therein. After complete mixing of the sample and reagent and complete neutralization of the alkalinity of the sample, the conductivity of the reagent treated sample ($E_2$) is measured by conductivity cell 100. As with the first conductivity measurement, the result is passed to the electronic analog calculator 109 and is also recorded by recorder 110.

After the second conductivity measurement by cell 100, a second increment of acid reagent is added to the sample through line 123 and fluid inlet 101. As with the first increment of reagent, the second reagent addition must be a carefully controlled known amount. It is preferred that the second increment of reagent equal the first increment inasmuch as this simplifies the subsequent computations and consequently allows the use of a simplified calculating device. Thus in the preferred apparatus, 0.3 ml. per min. of 3 Normal HCl is added at each acid reagent fluid inlet. If equal increments are not utilized, the second increment of reagent should be between one and two times the first.

Mixing of the second reagent increment with the sample is accomplished by means of a second mixing chamber 103 which is essentially identical to mixing chamber 99. After complete mixing of the second increment of reagent, the conductivity is measured a third time ($E_3$) by conductivity cell 104 and the result is transmitted to calculator 109 and also recorded by recorder 110. The water sample then passes to discharge 94.

Small amounts of $CO_2$ gas are liberated in the system as a result of the reaction of the acid reagent with the bicarbonate ion. In general, the amount of gas is insufficient to interfere with the measurement of the conductivity of the sample by conductivity cells 100 and 104, but the accumulation of the gas bubbles inside the system must nevertheless be prevented because an accumulation of gas could cause irregularities in the sample flow. Accordingly, the segment of the feed water sample flow line 93 which includes fluid inlets 98 and 101 and conductivity cells 100 and 104 is oriented in a vertical direction and a vent 105 is provided at the upper end of the vertically oriented segment.

The diameter of line 93 should be sufficiently large to allow air bubbles to be carried therethrough in order to prevent air blockages. An inside diameter of 3/16 inch is satisfactory. The diameter of the line should not be so large, however, that at ordinary rates of flow on the order of 300 ml. per min., the linear velocity of the sample becomes inordinately low. Under most circumstances a line having an inside diameter greater than ⅜ inch should not be used.

The rate of change of conductivity of the water sample after complete neutralization of the original alkalinity can be determined by the calculator from the second and third conductivity measurements. The hydrogen ion activity, and therefore the rate of change of conductivity of the sample after neutralization of the alkalinity thereof, is significantly affected by the background conductivity due to the presence of ions of neutral salts in the sample. By directly measuring the conductivity of the sample before and after the addition of the second increment of reagent, it is possible to compensate for such effects. Thus the background conductivity due to the presence of neutral salts such as sodium chloride or sulfate up to concentrations of about 800 parts per million has little or no effect on the alkalinity measurements made with the instant apparatus.

The total alkalinity of the original water sample may be computed from the amounts of acid reagent added in each increment, the initial background conductivity measured by cell 97, the rate of change of conductivity prior to neutralization of all of the alkalinity of the original sample, and the rate of change of conductivity after complete neutralization of all the alkalinity of the original water samples and the rate of flow of the water sample through the system. In applicants' preferred embodiment this may be achieved by utilizing an analog computer designed to solve the equation $$X = \frac{-(X_3 - X_2)(E_0 - E_3) - (X_3)(E_0 - E_2)}{M_i(X_3 - X_2) \cdot (E_3 - E_2)}$$

where $X$ is the alkalinity of the water sample, $E_0$ is the initial background conductivity of the water sample measured by conductivity cell 97, $E_2$ is the conductivity of the sample after the addition of the first increment of acid reagent through fluid inlet 98, $E_3$ is the conductivity of the sample after the addition of the second increment of acid reagent through fluid inlet 101, $X_2$ is the concentration of acid in the sample after the addition of the first increment of acid reagent through fluid inlet 98, $X_3$ is the concentration of acid in the sample after the addition of the second increment of acid reagent through fluid inlet and $M_i$ is the initial rate of change of conductivity of the water sample upon the addition of acid reagent prior to neutralization of the total alkalinity. Conventional commercially available analog computer components may be readily assembled or arranged into a system adapted to perform such calculations. Indeed, any of several approaches may be followed to achieve the desired result, and a wide variety of arrangements of electrical circuitry could be developed to perform the necessary calculations.

Figure 6:
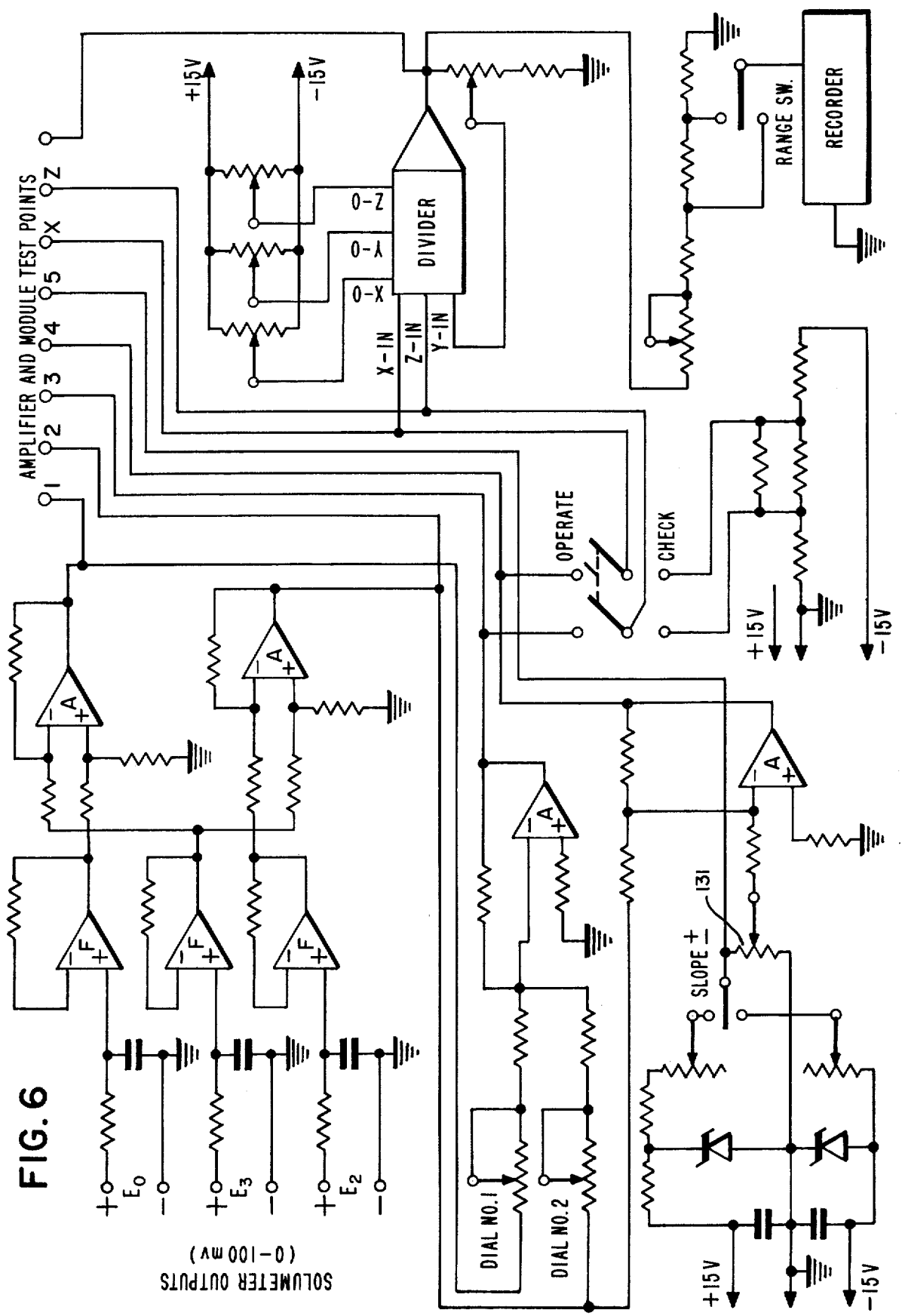
FIG. 6 is a schematic circuit diagram of an electronic calculator adapted for use with the apparatus of FIG. 5.

FIG. 6 illustrates one such arrangement. The three measured conductivity values are first passed through a filter network to reduce the noise level of the signals. The equation numerator and deonominator are then separately developed by operating amplifier stages and then are passed to a divider module for calculation of the final value. An attenuation stage may be provided to match the divider output to the output device or recorder. The acid concentrations are represented in the amplifier circuitry by appropriate resistances. Fixed resistances may be utilized if the acid concentrations remain relatively stable, but the use of variable resistances allows for precise calibration of the apparatus. A variable resistance (slope adjustment) 131 is also provided to adjust the rate of change of the conductivity of the original water sample upon the addition of reagent. The proper setting may be determined by titrating the alkalinity of a sample by conventional procedures and then adjusting the variable slope resistance until the output value (X) from the calculator equals the titrated value. Dummy inputs are provided for checking the calculator. Commercially available amplifiers and divider module components may be utilized. In the arrangement illustrated in FIG. 6, the follower amplifiers are one-half Signetics No. 5558, the operational feedback amplifiers are type $\mu$A741 and the divider module is an Intersil No. 8013. An optional range switch may be included to set the the calculator for what ever range of conductivities may be encountered in the system.

The calculator generates a continuous output signal directly proportional to the alkalinity of the original sample. The resulting alkalinity value is then passed to output device 111 and is also transmitted to recorder 110 where it is recorded on a strip chart. The output may be utilized to control the addition of treatment chemicals to the water supply, to set off an alarm or to shut down apparatus when prescribed limits of alkalinity are exceeded.

Increased sensitivity is possible because the apparatus takes advantage of the high mobility and conductivity of hydronium and hydroxide ions in aqueous systems.

The calculator may also be designed to shut down the monitor and/or set off an alarm in the event of failure of the reagent supply system. This is most readily effected by carrying out a direct comparison of the second and third conductivity measurements. The addition of more reagent or the dilution of the reagent treated sample will result in or change in the measured conductivity. Therefore if $E_3$ equals $E_2$, it is an indication that the reagent supply system is not functioning, so that the monitor should be shut down. A sudden change of ($E_3 - E_2$) may also indicate failure of the reagent supply system.

In an alternative mode of operation, valve 124 is closed and the flow of acid reagent through fluid inlet 98 is increased until it is approximately equal to the combined reagent flow through inlets 98 and 101 in the normal mode of operation, i.e. about 0.6 ml. per min. Valve 127 is opened so that a portion of the boiler feed water sample bypasses fluid inlet 98 and conductivity cell 100 and enters the main sample flow line 93 through fluid inlet 102. By means of valves 95 and 127 and flowmeters 96 and 128 the relative proportion of the sample passing through each of the respective lines, and consequently the dilution of the sample flowing through the main sample line 93 by the portion of the sample flowing through bypass line 125, may be controlled. Preferably they should be equalized. By substituting the conductivity value measured by conductivity cell 104 for the conductivity reading taken after the addition of the first increment of acid reagent in the normal mode of operation and the conductivity reading taken by conductivity cell 100 for the conductivity value measured after the addition of the second increment of acid reagent in the normal mode of operation, the determination of the total alkalinity of the water sample may be effected in substantially the same manner as previously described for the normal mode of operation. The substitution of conductivity values may be effected by switching the wires connecting conductivity meters 107 and 108 to the electronic calculator 109 or by means of a changeover switch. The concentration of acid after the addition of reagent should be substituted for the concentration of acid after the addition of the second increment of acid reagent in the normal mode of operation and the concentration of acid after dilution of the sample flowing through line 93 with sample from bypass line 125 should be substituted for the concentration of acid after the addition of the second reagent increment in the normal mode of operation. The acid concentrations are readily derived from the initial concentration of the reagent, the rate of flow of reagent through supply line 112 and the rates of flow of the water sample through lines 93 and 125.

The foregoing apparatus is also useful for determining the acidity of weakly acidic solutions, such as boric acid, by using an alkaline reagent such as sodium hydroxide (NaOH) and making similar conductivity measurements.

The foregoing apparatus having a sample flow rate of approximately 300 ml. per min. and utilizing 3 Normal hydrochloric acid reagent at a flow rate of 0.6 ml. per min. and conductivity cells having cell constants of 10 is specifically adapted to monitor the alkalinity of a municipal water supply in the range of 10 to 200 ppm expressed as $CaCO_3$. By decreasing the reagent concentration and by utilizing conductivity cells with smaller cell constants ranging down to about 0.10, the apparatus may be readily modified to measure alkalinities in the 0 to 10 ppm range expressed $CaCO_3$. Thus the apparatus may also be used for monitoring the alkalinity of cooling tower water, boiler feed water, or turbine condensate.

In the apparatus of FIG. 5, no special means are required for temperature control because at the flow rates utilized, i.e. approximately 300 ml. per min. sample and 0.6 ml. per min. reagent, only minimal temperature changes occur in the sample in passing through the apparatus.

The efficacy of the invention is further demonstrated by the following tests:

Test II

Water samples from the Vermilion Generating Station of the Illinois Power Company in Danville, Illinois, were analyzed for alkalinity by adding a controlled excess amount of strong acid and measuring the electrical conductivity ($l_1$). An identical amount of acid was added to a sample of deionized condensate and the electrical conductivity ($l_0$) was measured to provide a standard value for comparison. The differential conductivity ($\Delta L^1$) was determined by subtracting the measured conductivity of each sample from the standard value. Thus $\Delta L^1 = l_0 - l_1$. The alkalinity expressed in terms of milligrams of $CaCO_3$ per liter was calculated from the $\Delta L^1$ value for each sample. For comparison purposes the alkalinity of each sample was also determined by conventional colorimetric titration procedures. The results of the tests are listed in Table II.

Table II

| Sample Source | Differential Conductivity $\Delta L^1$ mhos | Calculated Alkalinity mg. $CaCO_3$/l | Titrated Alkalinity mg. $CaCO_3$/l |
|---|---|---|---|
| Main Steam | 5.00 | .56 | .56 |
| Main Steam | 5.75 | .64 | .58 |
| Turbine Cond. Steam | 4.00 | .45 | .45 |
| Feedwater | 8.40 | .93 | .95 |

Test III

Figure 7:
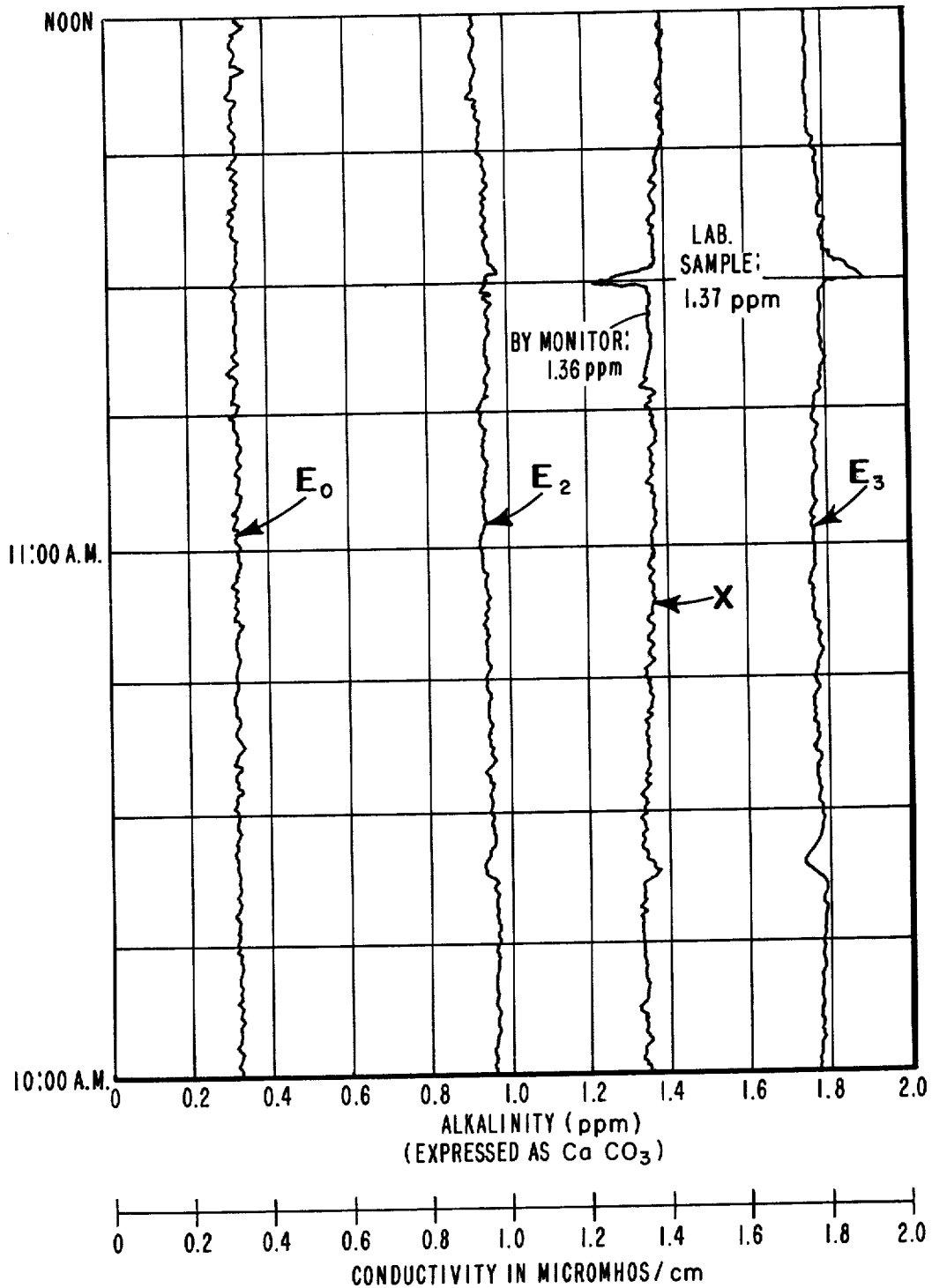
FIGS. 7 and 8 are graphs showing the results of tests conducted with the apparatus of FIG. 5.

The alkalinity of turbine condensate from the No. 4 Turbine of Ridgeland Station of Commonwealth Edison at Stickney, Illinois was continuously monitored using apparatus of the type disclosed in FIG. 5 by withdrawing a continuous sample, measuring the electrical conductivity of the sample ($E_0$), adding a controlled excess amount of acid to the sample and mixing, measuring the conductivity of the sample with the acid ($E_2$), adding a second controlled amount of acid and mixing, and again measuring the conductivity of the sample ($E_3$). The measured conductivity values were fed to an analog computer prorammed to solve the equation $$X = \frac{-(X_3 - X_2)(E_0 - E_3) - (X_3)(E_3 - E_2)}{(M_i)(X_3 - X_2) - (E_3 - E_2)}$$

where $X$ is the differential conductivity equivalent of the alkalinity, $X_2$ and $X_3$ are the acid concentrations after the first and second acid additions, $M_i$ is the initial rate of change of conductivity of the sample upon the addition of acid, and $E_0$, $E_2$ and $E_3$ are the measured conductivity values. The measured conductivity values and the calculated alkalinity were continuously recorded on a multiple chart recorder. A representation of a two hour segment of a chart covering an interval from 10 a.m. to noon is shown in FIG. 7. The figure shows a gradual increase in alkalinity from about 1.33 ppm (expressed as $CaCO_3$) at 10:00 a.m. to about 1.40 ppm at noon. The sharp discontinuity in the recorded values at about 11:30 a.m. was caused by the taking of a sample for laboratory confirmation by conventional colorametric titration techniques. The laboratory test yielded an alkalinity of 1.37 ppm $CaCO_3$ as compared to a value of 1.36 ppm $CaCO_3$ determined according to the invention.

Test IV

Figure 8:
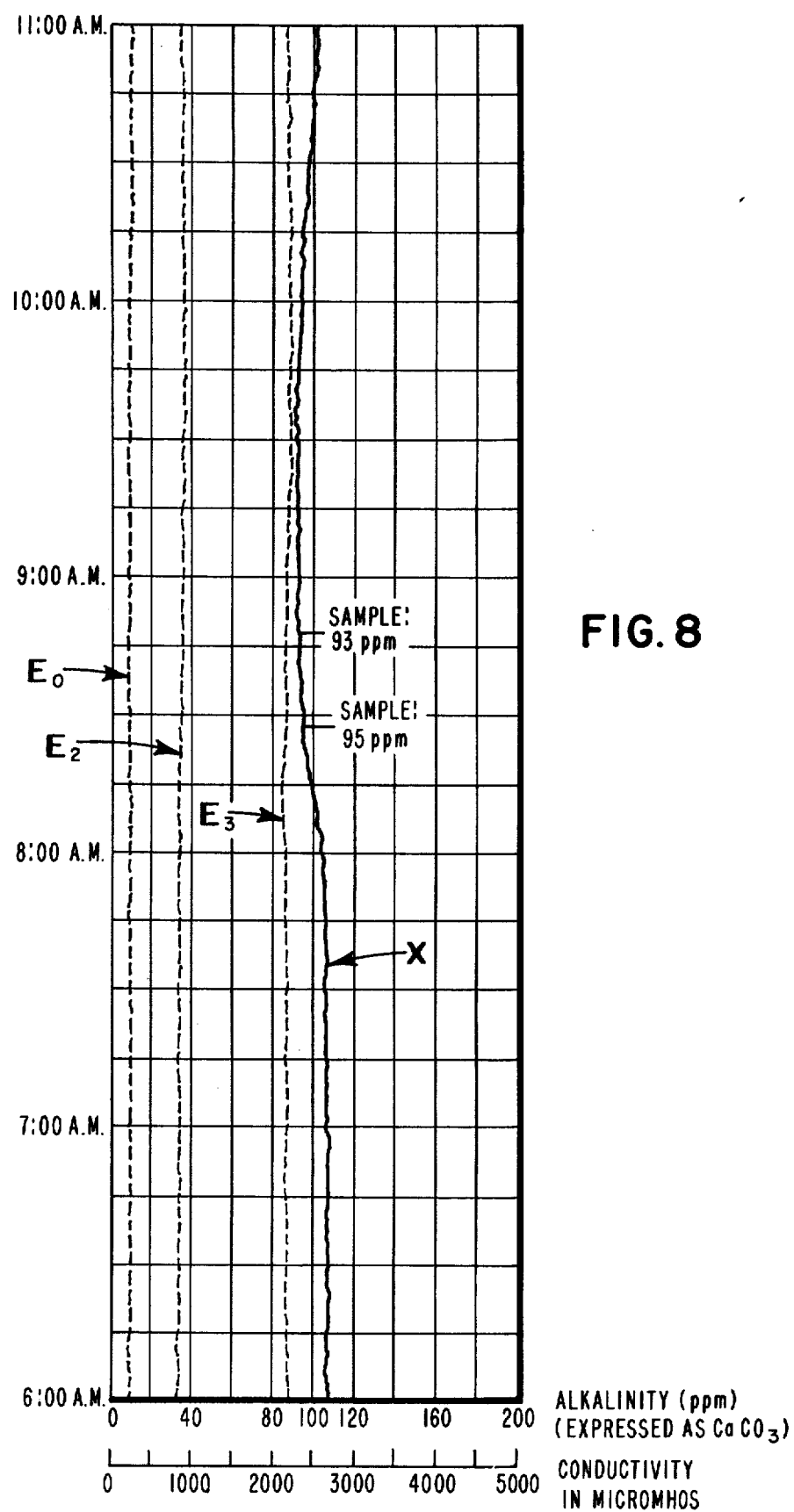

The alkalinity of tap water from the Champaign-Urbana, Illinois Municipal Water Supply was continuously monitored at a remote monitoring point in the distribution system with the apparatus of FIG. 5 according to the procedure described above under Test III, Champaign-Urbana Municipal water is lime softened and post-treated with sulfuric acid to prevent clogging of the sand filters and deposition of excess calcium carbonate in the distribution system. A disruption of the acid feed system at the treatment plant was later detected at the remote monitoring point by an increase in pH and a corresponding decrease in alkalinity. FIG. 8 shows measured conductivity values and calculated alkalinity for a five hour time interval from 6 a.m. to 11 a.m. The figure shows that the alkalinity maintained a relatively stable level of about 107 ppm (expressed as $CaCO_3$) from 6:00 to 8:00 a.m. The alkalinity then started to drop and reached a minimum value of about 90 ppm between 9:15 and 9:30 a.m. Thereafter the alkalinity started to rise gradually toward normal levels, reaching a value of about 103 ppm at 11:00 a.m. To confirm the results, samples of the water were taken at about 8:27 a.m. and 8:48 a.m. and titrated by conventional colorimetric techniques to a methyl orange endpoint. The titration of the first sample yielded an alkalinity of 95 ppm which corresponded exactly to the alkalinity measured according to the invention. The titration of the second sample yielded an alkalinity value of 93 ppm which likewise corresponded to the alkalinity measured according to the invention.

The foregoing arrangements have been described merely as illustrations of the apparatus of the invention. The invention is not limited to use in steam generator systems or nuclear reactors or even aqueous systems in general, but is applicable for measuring the presence of weak acids or bases in liquid systems of all types. Modifications of the invention undoubtedly will occur to those skilled in the art, therefore, the scope of the invention is to be limited solely by the scope of the appended claims.

We claim:

1. Apparatus for measuring the acidity or alkalinity of water comprising:
    a. a flow line for a sample of the water to be measured;
    b. means to control the rate of flow of said water sample through said line;
    c. a first conductivity cell on said line adapted to measure the electrical conductivity of a water sample flowing through said line;
    d. a first fluid inlet downstream from said first conductivity cell on said line for adding a controlled proportion of reagent to a water sample flowing through said line;
    e. a second conductivity cell downstream from said first fluid inlet for measuring the electrical conductivity of a water sample flowing through said line after the addition of a controlled proportion of reagent;
    f. a second fluid inlet downstream from said second conductivity cell on said line for adding a controlled proportion of a liquid to a water sample flowing through said line;
    g. a third conductivity cell downstream from said second fluid inlet on said line for measuring the electrical conductivity of a water sample flowing through said line after the addition of a controlled proportion of liquid; and
    h. an electronic calculator connected to said first, second and third conductivity cells and adapted to generate an output signal indicative of the acidity or alkalinity of a water sample flowing through said line.

2. An apparatus as recited in claim 1 further comprising means between said first fluid inlet and said second conductivity cell on said line for uniformly mixing reagent added through said first fluid inlet with a sample flowing through said line.

3. An apparatus as recited in claim 1 further reciting means located between said second fluid inlet and said third conductivity cell on said line for uniformly mixing liquid added through said second fluid inlet with a water sample flowing through said line.

4. Apparatus as recited in claim 1 wherein said means to control the rate of flow of a water sample through said line comprises a flow meter and a valve on said line.

5. Apparatus as recited in claim 1 further comprising a bypass line connected to said flow line upstream from said first conductivity cell and to said second fluid inlet, and means on said bypass line for regulating the flow of water sample therethrough.

6. Apparatus as recited in claim 1 further comprising first, second and third conductivity meters connected to said first, second and third conductivity cells respectively, and a multiple chart recorder connected to said first, second and third conductivity meters and to said electronic calculator.

7. Apparatus as recited in claim 1 wherein said first fluid inlet, said second conductivity cell, said second fluid inlet and said third conductivity cell are all disposed on a single, vertically oriented segment of said flow line, and a gas vent is provided at the top of said vertical line segment.

8. Apparatus as recited in claim 1 wherein said electronic calculator comprises an analog computer adapted to calculate the alkalinity of the water sample from the conductivity values measured by the conductivity cells, the reagent concentrations and the initial rate of change of conductivity of the original sample upon the addition of reagent.

9. Apparatus as recited in claim 8 wherein said analog computer further comprises means to adjust the computer to varying rates of change of conductivity due to the presence of different species in the original sample.

10. Apparatus as recited in claim 1 further comprising a reagent constant head device having a supply chamber, a return chamber adapted to receive excess reagent overflowing from said supply chamber, a supply line from said supply chamber to said first fluid inlet, a reagent reservoir, a fill line from said reagent reservoir to said supply chamber, pump means on said fill line for transferring reagent from said reagent reservoir to said supply chamber and a return line from said return chamber to said reagent reservoir.

11. Apparatus as recited in claim 10 further comprising a connecting line connecting said reagent supply line and second fluid inlet, and valve means on said connecting line for regulating the flow of reagent therethrough.

12. An apparatus as recited in claim 1 further comprising means for controlling the level of dissolved carbon dioxide in a water sample flowing through said line.

13. Apparatus as recited in claim 12 wherein said means to control the level of dissolved carbon dioxide comprises a carbonating apparatus adapted to adjust the pH of a water sample flowing through said line to a pH from about 5 to 8.

14. Apparatus as recited in claim 13 wherein said carbonating apparatus is adapted to adjust the pH of a water sample flowing through said line to a pH from about 7 to 8.

15. Apparatus for measuring the acidity or alkalinity of water comprising:
a. a flow line for a sample of the water to be measured;
b. means to control the rate of flow of said water sample through said line;
c. a first conductivity cell on said line adapted to measure the electrical conductivity of a water sample flowing through said line;
d. a first reagent adding means downstream from said first conductivity cell on said line for adding a first controlled proportion of reagent selected from the class consisting of acids and bases which are 100% dissociated in aqueous solution, to a water sample flowing through said line;
e. a second conductivity cell downstream from said first reagent adding means for measuring the electrical conductivity of a water sample flowing through said line after the addition of said first controlled proportion of reagent;
f. a second reagent adding means downstream from said second conductivity cell on said line for adding a second controlled proportion of reagent selected from the class consisting of acids and bases which are 100% dissociated in aqueous solution, to a water sample flowing through said line;
g. a third conductivity cell downstream from said second reagent adding means on said line for measuring the electrical conductivity of a water sample flowing through said line after the addition of said second controlled proportion of liquid; and
h. an electronic calculator connected to said first, second and third conductivity cells and adapted to generate an output signal indicative of the initial acidity or alkalinity of a water sample flowing through said line.

* * * * *